(12) United States Patent
Burcham

(10) Patent No.: US 8,299,059 B2
(45) Date of Patent: Oct. 30, 2012

(54) CRYSTALLINE COMPOUND AND A PROCESS FOR ITS PREPARATION

(75) Inventor: Christopher Luis Burcham, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 88 days.

(21) Appl. No.: 12/915,714

(22) Filed: Oct. 29, 2010

(65) Prior Publication Data

US 2011/0105471 A1 May 5, 2011

Related U.S. Application Data

(60) Provisional application No. 61/256,475, filed on Oct. 30, 2009.

(51) Int. Cl.
*C07D 223/16* (2006.01)
*A61K 31/55* (2006.01)
(52) U.S. Cl. .................. 514/212.07; 540/523
(58) Field of Classification Search ............ 540/523; 514/212.07
See application file for complete search history.

(56) References Cited

U.S. PATENT DOCUMENTS 7,468,365 B2 * 12/2008 Audia et al. ............. 514/212.07

OTHER PUBLICATIONS

Podczeck, et al., "The influence of particle size and shape on the angle of internal friction and the flow factor of unlubricated and lubricated powers" Int. J. Pharma, 144, 187-194, (1996).
Tan and Newton, "Powder flowability as an indication of capsule filling performance" Int. J. Pharm, 61, 145-155 (1990).
Francesco Panza et al., Gamma-secretase inhibitors for treating Alzheimer's disease: rationale and clinical data, Clinical Investigation, (2011), 1175-1194, vol. 1(8).

* cited by examiner

*Primary Examiner* — Bruck Kifle
(74) *Attorney, Agent, or Firm* — Nelsen L. Lentz; Tonya L. Combs; Elizabeth Dingess-Hammond

(57) ABSTRACT

A form of crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II having improved flowability and drug-loading properties and a process for its preparation.

6 Claims, No Drawings

CRYSTALLINE COMPOUND AND A PROCESS FOR ITS PREPARATION

The present invention is in the field of treatment of Alzheimer's disease and other diseases and disorders involving amyloid β(Aβ) peptide. Semagacestat is (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide and it is taught to be useful for treating such diseases and disorders. See U.S. Pat. No. 7,468,365.

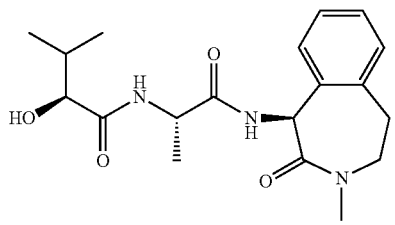

Semagacestat

Semagacestat is known to exist in a number of polymorphic forms, including a dihydrate and at least two anhydrate forms, designated as anhydrate Form I or α and anhydrate Form II or β. Id. Semagacestat anhydrate Form II is the preferred crystalline form of semagacestat.

Active pharmaceutical ingredient and drug product powders should have good flow characteristics in order to be easily and consistently transferred from one process unit operation to another and to enable tablet and capsule drug products to be prepared with consistent and accurate weights. The preferred dosage form for semagacestat is a small tablet to facilitate administration to a geriatric, or Alzheimer's, population. Furthermore, the preferred therapeutic dose is delivered in a single dosage form with a drug-load greater than 30% by weight of the formulation.

When semagacestat is crystallized as described in the prior art as anhydrate Form II, long, thin needle-like particles are formed with an average aspect ratio of about 5:1 to 20:1. The flow properties of the needle-like particles of semagacestat anhydrate Form II make it less optimal to be consistently processed for accurate tablet and capsule production. Specifically, the needle-like particles are not suitable to prepare a tablet with a drug-load greater than 30% with consistent uniformity of dosage units within acceptable ranges of formulation standards. See US Pharmacopeia 32-National Formulary 27 (USP32/NF27), Chapter 905, Uniformity of Dosage Units (2009).

In order to obtain free flowing materials, the aspect ratio of particles should be less than 5:1. See Podczeck, et. al., Int. J. Pharm. 144, (1996) 187-194. If long, needle-like particles are simply milled to reduce aspect ratio, the final particle size is too fine which also results in a poor flowing material. See Tan and Newton, Int. J. Pharm, 61, (1990) 145-155. Therefore, particles that possess a small aspect ratio and a large particle size are needed to facilitate processing and accommodate the preferred dosage form. The present invention provides semagacestat anhydrate Form II in a new crystal habit which exhibits improved physical properties over previously known crystalline semagacestat anhydrate Form II materials, including improved flowability properties, higher drug-loading potential, and more consistent uniformity of dosage unit.

The present invention provides crystalline semagacestat anhydrate Form II wherein the $x_{10}$ is between 4 μm and 50 μm, the $x_{50}$ is between 25 μm and 100 μm, and the $x_{90}$ is between 80 μm and 250 μm. Preferably, the $x_{10}$ is greater than 9 μm and the $x_{50}$ is greater than 50 μm.

The present invention provides crystalline semagacestat anhydrate Form II having a crystal habit characterized by an average length-to-width aspect ratio of less than or equal to 5:1. Preferably, the average aspect ratio is less than 5:1. More preferably, the average aspect ratio is less than or equal to 3:1.

The present invention also provides crystalline semagacestat anhydrate Form II characterized by a crystal habit having an average length-to-width aspect ratio of less than or equal to 5:1 and a particle size distribution wherein the $x_{10}$ is less than 50 μm, the $x_{50}$ is less than 100 μm, and the $x_{90}$ is less than 250 μm. In said embodiment, the present invention further provides crystalline semagacestat anhydrate Form II wherein the $x_{10}$ is greater than 4 μm and the $x_{50}$ is greater than 25 μm. Further in said embodiments, the average length-to-width aspect ratio is less than 5:1. Further in said embodiments, the present invention provides the average length-to-width aspect ratio is less than or equal to 3:1.

A preferred embodiment of the present invention provides crystalline semagacestat anhydrate Form II characterized by a crystal habit having an average length-to-width aspect ratio of less than or equal to 5:1 and a median particle size of 25 to 100 μm, wherein the $x_{10}$ is greater than 4 μm. In said embodiment, the present invention also provides the average length-to-width aspect ratio is less than 5:1. Further in said embodiments, the present invention provides the average length-to-width aspect ratio is less than or equal to 3:1. Further in said embodiments, the present invention provides crystalline semagacestat anhydrate Form II wherein the $x_{90}$ is less than 250 μm.

The present invention further provides a pharmaceutical formulation comprising crystalline semagacestat anhydrate Form II characterized by a crystal habit having an average length-to-width aspect ratio of less than or equal to 5:1 and a particle size distribution wherein the $x_{10}$ is less than 50 μm, the $x_{50}$ is less than 100 μm, and the $x_{90}$ is less than 250 μm, and a pharmaceutically acceptable carrier, diluent, or excipient. In said embodiment, the present invention also provides the average length-to-width aspect ratio is less than 5:1. Further in said embodiments, the present invention provides the average length-to-width aspect ratio is less than or equal to 3:1. In said embodiments, the present invention further provides crystalline semagacestat anhydrate Form II wherein the $x_{10}$ is greater than 4 μm and the $x_{50}$ is greater than 25 μm. Further, in said embodiments, the drug loading is 30% or greater and the tablet weight variation is 3.39% or less. Even further, in said embodiments, the drug loading is 35%.

Furthermore, this invention provides a method of treating Alzheimer's disease by administering an effective amount of semagecestat anydrate form II characterized by a crystal habit having an average length-to-width aspect ratio of less than or equal to 5:1 and a particle size distribution wherein the $x_{10}$ is less than 50 μm, the $x_{50}$ is less than 100 μm, and the $x_{90}$ is less than 250 μm. In said embodiment, the present invention also provides the average length-to-width aspect ratio is less than 5:1. Further in said embodiments, the present invention provides the average length-to-width aspect ratio is less than or equal to 3:1.

The present invention also provides semagacestate anhydrate form II characterized by a crystal habit having an average length-to-width aspect ratio of less than or equal to 5:1 and a particle size distribution wherein the $x_{10}$ is less than 50 μm, the $x_{50}$ is less than 100 μm, and the $x_{90}$ is less than 250 μm for use in therapy. In said embodiment, the present invention also provides the average length-to-width aspect ratio is less than 5:1. Further in said embodiments, the present invention provides the average length-to-width aspect ratio is less than or equal to 3:1.

Further, this invention provides semagacestat anydrate form II characterized by a crystal habit having an average length-to-width aspect ratio of less than or equal to 5:1 and a particle size distribution wherein the $x_{10}$ is less than 50 μm, the $x_{50}$ is less than 100 μm, and the $x_{90}$ is less than 250 μm for the treatment of Alzheimer's disease. In said embodiment, the present invention also provides the average length-to-width aspect ratio is less than 5:1. Further in said embodiments, the present invention provides the average length-to-width aspect ratio is less than or equal to 3:1.

Even further, this invention provides the use of semagacestat anhydrate form II characterized by a crystal habit having an average length-to-width aspect ratio of less than or equal to 5:1 and a particle size distribution wherein the $x_{10}$ is less than 50 μm, the $x_{50}$ is less than 100 μm, and the $x_{90}$ is less than 250 μm for the manufacture of a medicament for the treatment of Alzheimer's disease. In said embodiment, the present invention also provides the average length-to-width aspect ratio is less than 5:1. Further in said embodiments, the present invention provides the average length-to-width aspect ratio is less than or equal to 3:1.

The present invention provides a process for preparing crystalline semagacestat anhydrate Form II characterized by a crystal habit having an average length-to-width aspect ratio of less than or equal to 5:1 and a particle size distribution wherein $x_{10}$ is less than 50 μm, the $x_{50}$ is less than 100 μm, and the $x_{90}$ is less than 250 μm comprising the steps of:

a. Providing a solution of (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide in a suitable solvent matrix;

b. Cooling the solution;

c. Optionally seeding by adding seed crystals to form a suspension;

d. Thermal cycling of the suspension wherein the suspension is heated to a temperature to redissolve the solids of the suspension and cooled at a controlled rate to crystallize the compound to form a subsequent suspension; and e. Isolating crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II.

In said embodiment, the present invention also provides the average length-to-width aspect ratio is less than 5:1. Further in said embodiments, the present invention provides the average length-to-width aspect ratio is less than or equal to 3:1.

Any form of semagacestat, including solvates and hydrates, can be used as a starting material for the process of the present invention. For example, any of the known forms of semagacestat can be used: the dihydrate, the anhydrate Form I, or the anhydrate Form II.

Solvents useful for the process of the invention include those that increase the solubility of semagacestat anhydrate form II with increasing temperature, have a boiling point above 45° C., and are pharmaceutically acceptable per ICH guidelines. See ICH Harmonized Tripartite Guideline, 1997. "Impurities: Guideline for Residual Solvents Q3C." International Conference on Harmonization of Technical Requirements for Registration of Pharmaceuticals for Human Use. Herein, the use of the term "solvent matrix" refers to a single solvent or a mixture of solvents. Examples of such solvents include isopropyl alcohol, ethanol, methanol, acetonitrile, tetrahydrofuran, methyl ethyl ketone, or mixtures thereof. Water can also be used in volumes less than 60-70% of total volume of the solvent matrix. Preferably, the solvent is isopropyl alcohol. Most preferably, the solvent is a mixture of isopropyl alcohol and water. In said embodiment, the water content is preferably less than 5% by weight.

The crystallizer may be cooled using a cubic cooling ramp, a single linear cooling ramp, or a series of linear cooling ramps. The cubic cooling ramp is programmed according to the following equation:

$$T(t) = T_i - (T_i - T_f)\left(\frac{1}{\tau}\right)^3$$

where T(t) is the temperature at time t, $t_i$ and $T_f$ are the initial and final temperatures, respectively, and τ is the overall cycle cooling time. Preferably, a series of linear ramps can be used to approximate the cubic cooling curve.

In the process of the present invention, the initial solution of semagacestat in a suitable solvent matrix is cooled so that semagacestat will crystallize from the solution to provide a suspension. Preferably, upon cooling at least 5% of the compound is crystallized.

Crystallization is initiated or enhanced by seeding or primary-nucleation. Preferably, crystallization is initiated by seeding. Seeding can be achieved by adding a seed load of up to 50% by weight. Preferably, crystallization is initiated by adding a seed load of 0.01% to 2%. Most preferably, crystallization is initiated by adding a seed load of 1%. The particle size of the seed is an $x_{90}$ of up to 500 μm. The particle size of the seed is preferably an $x_{90}$ of less than 250 μm. The particle size of the seed is more preferably an $x_{90}$ of less than 200 μm. The seed is added either as a slurry in the appropriate solvent or as a dry powder. Preferably the seed is added as a slurry. An appropriate solvent to prepare the seed slurry is one that is miscible with the solvent matrix and in which semagacestat is completely or partially soluble. Preferably the solvent is isopropyl alcohol. The temperature of the seed point is such that the system is supersaturated or is below the dissolution temperature from about 55° C. to 75° C. Most preferably, the temperature of the seed point is between 72 and 75° C.

After seeding is complete, cooling of the suspension can be employed so that further crystallization of semagacestat can be achieved. Preferably, about 50% of semagacestat is crystallized.

The crystal habit of semagacestat is manipulated using thermal cycling conditions. The temperature of the crystallizer is increased to a temperature of about 50 to 75° C. where about 25 to 95% of the solids are dissolved. Preferably, about 50% of the solids are dissolved. Once the desired solution saturation is reached, the crystallizer is cooled, preferably back to the initial temperature. The rate of cooling is controlled over 30 minutes or longer to minimize secondary nucleation. Preferably, the temperature of the crystallizer is heated to 65° C. and maintained at 65° C. until solids are no longer dissolving, and cooled to 45° C. over 1.5 hours. The thermal cycle can be repeated more than once if necessary or desired. Preferably, the process is repeated three times. Preferably, prior to thermal cycling, the crystallized material is milled to a finer particle size. Milling can be achieved by use of wet or slurry mills, such as high shear mixers, homogenizers, colloid mills, or by the use of sono-milling.

After thermal cycling is completed, anti-solvent can be added to increase yield and to maintain the correct crystal form during filtration and drying. Examples of anti-solvents for semagacestat include solvents in which semagacestat has low solubility. Furthermore, the anti-solvent(s) are miscible with the solvent matrix and are pharmaceutically acceptable per ICH guidelines, such as heptanes, n-heptane, toluene, tert-butyl methyl ether, cyclohexane, chlorobenzene, amyl acetate, hexanes, n-hexane, or mixtures thereof. A preferred anti-solvent is n-heptane.

The particle size of the crystals is reduced by milling via wet mills prior to isolation or dry mills after isolation. Multiple milling techniques can be employed, such as conical mills, universal mills, pin mills, jet mills, turbo rotor mills, hammer mills, knife mills, and the like. Preferably, the particle size of the crystals is reduced via a slurry mill prior to filtration. The crystallizer can be cooled to room temperature prior to milling and filtration and drying. If wet mills are used, crystals of semagacestat are dried prior to the delumping step. If dry mills are used, delumping is unnecessary.

Crystals of semagacestat are delumped using a delumping mill, such as a conical mill, a hammer mill, or a knife mill, which act to delump particles without reducing the individual particle size. Preferably, a conical mill is used.

The term "dosage unit" is a dosage form containing a single dose or part of a dose of drug substance in each unit.

The term "uniformity of dosage unit" is the degree of weight variation or content uniformity in the amount of the drug substance among dosage units.

The term "content uniformity" is a measure used for providing the uniform distribution of the active content in a production batch. It is performed by measuring the active content of n individual dosage units.

The term "aspect ratio" is the major axis dimension of a particle (length) divided by minor axis dimension (width).

The term "API" refers to active pharmaceutical ingredient.

The term "flowability" refers to the ease at which a powder or bulk solid flows. To assess powder flowability, the powder sample is measured using an annular shear tester, such as the Schulze Ring Shear Tester.

The term "FFC" refers to flow factor coefficient. FFC is a dimensionless number that is the ratio of the major consolidation stress to the unconfined yield stress. The larger the FFC value, the better a bulk solid flows.

The term "seed load" refers to the weight of seed relative to the total weight of semagacestat.

The term "seed point" refers to the point when seed is added to induce crystallization.

The term "$x_{10}$" refers to a value of a cumulative volume distribution (undersized). The $x_{10}$ value is the particle size wherein 10% of the population (by mass or volume) is smaller than the quoted number (as measured by the equivalent spherical diameter).

The term "$x_{50}$" refers to a value of a cumulative volume distribution (undersized). The $x_{50}$ value is the particle size wherein 50% of the population (by mass or volume) is smaller than the quoted number (as measured by the equivalent spherical diameter). This is also referred to as the median particle size.

The term "$x_{90}$" refers to a value of a cumulative volume distribution (undersized). The $x_{90}$ value is the particle size wherein 90% of the population (by mass or volume) is smaller than the quoted number (as measured by the equivalent spherical diameter).

The term "thermal cycling" refers to increasing the solution temperature in the crystallizer at a defined rate, optionally holding the temperature at a maximum temperature, and decreasing the temperature at a defined rate.

The term "ICH" refers to International Conference on Harmonization of Technical Requirements for Registration of Pharmaceuticals for Human Use.

The term "SSA" refers to specific surface area.

The term "BET" refers to BET theory which is a well-known model for the physical adsorption of gas molecules on a solid surface that is the basis for the measurement of the specific surface area of a material. See Brunauer, et. al., *J. Am. Chem. Soc.*, 1938, 60, 309.

EXAMPLE 1

Crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide (80 kg, 221 mol) is added to isopropyl alcohol (324 kg, 5.16 volumes). The slurry is heated to 78° C. and purified water (12 kg, 0.15 volumes) is added. The mixture is held at 78° C. until all solids have dissolved. The solution is cooled to 72° C. over 30 minutes to ensure supersaturation. The saturation temperature at this composition is 77° C.

TABLE 1

| Item | Amount | Units | Eq./Vol. Eq. | Mass Fraction |
|---|---|---|---|---|
| semagacestat | 80 | kg | 1 eq | 19.2% |
| water | 12 | kg | 0.15 vol | 2.89% |
| isopropyl alcohol | 403 | L | 5.16 vol | 77.9% |

Table 1 illustrates the composition prior to seeding for a batch size of 80 kg of semagacestat.

Seed compound is prepared according to the procedure in U.S. Pat. No. 7,468,365. A seed slurry is prepared by first adding isopropyl alcohol (1.25 kg, 0.02 volumes) into a polypropylene carboy. Next, semagacestat seed (0.8 kg, 0.01 molar equivalents) is charged to the carboy. The slurry is prepared 10 minutes or less prior to seeding in order to minimize the conversion from Form II anhydrate to Form I anhydrate. The seed slurry is transferred to the crystallizer to initiate crystallization. After seeding, the suspension is stirred and held for no more than 10 minutes. The crystallizer contents are cooled to 45° C. over 6 h.

The suspension is transferred through an IKA® DRS 2000/10 slurry mill using a flow meter to regulate the flow to less than 40 kg/min from the crystallizer to a receiver tank. The mill is configured with three fine heads and is operated at a tip speed of 22.7 m/s. Typical flow rates range between 20 to 30 kg/min.

After milling is complete, the suspension is heated to 65° C. over 30 minutes and maintained at 65° C. for 45 minutes. At this temperature, approximately 50% of the solids are put back into solution. The temperature is decreased to 45° C. over 90 minutes to grow the remaining crystals and avoid nucleation. The suspension is maintained at 45° C. for 30 minutes to ensure that crystal growth is complete. The cycle is repeated three times.

N-heptane (372 kg, 6.8 volumes) is charged into a separate reactor and heated to 45° C. The heptane is transferred to the crystallizer over 90 minutes to complete crystallization. The slurry is cooled to 17° C. over 120 minutes. The suspension is transferred through an IKA® DRS 2000/10 slurry mill using a flow meter to regulate the flow to less than 40 kg/min from the crystallizer to a receiver tank. The mill is configured with three fine heads and is operated at a tip speed of 32.0 m/s. The flow rate ranges between 20 to 30 kg/min. A sample of the milled suspension is collected from the discharge of the mill and assayed by laser diffraction for particle size.

The product is filtered on an agitated filter dryer. N-heptane (136 kg, 3 volumes) is charged into a wash solvent tank. The filter cake is washed with n-heptane. Nitrogen is purged through the system for 60 minutes or longer to deliquor the cake with the dryer temperature maintained at 55° C. Vacuum is applied. The cake is agitated for short durations periodically during drying. Drying is complete when the loss on drying is less than 2 wt %. Once dry, the product is discharged from the dryer and delumped with a Quadro® U20 Comil through a 1.15 mm round hole screen. The mill is operated at a top speed of 8.4 m/s. The milled material is drum rolled to ensure homogeneity. The yield for the overall process is 88-92%.

Method 2

Traditional Recrystallization Method

Crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide dihydrate (6 kg, 15.1 mol) is added to 55.2 L (9.2 volumes) of isopropyl alcohol. The mixture is heated to 70° C. to ensure dissolution. Once dissolved, the mixture is heated to reflux and 28 L (4.6 volumes) of solvent distilled, generating a saturated solution at reflux. The solution is seeded with 0.5% wt semagacestat (0.03 kg). The suspension is held for 1 h, followed by the addition of 36 L (6 volumes) of n-heptane (anti-solvent) added over 3 h. Distillation is used to remove an additional 33.6 L (5.6 vol) of solvent. The crystallizer is cooled from reflux (about 78° C.) to 25° C. over 2 h, held for 1, filtered, and dried. After drying, the isolated solids are milled with a Quadro Comil through a 230 µm round hole screen.

Analytical Techniques

Determination of Particle Size Distribution Product by Laser Diffraction

Laser diffraction particle size analysis is employed to determine the $x_{10}$, $x_{50}$ and $x_{90}$ values. The procedure uses Fraunhofer laser diffraction theory to calculate the particle size distribution. The analysis is performed with a Malvern Mastersizer 2000 equipped with a Hydro 2000S wet module. A filtered (0.22 µm) solution composed of 0.35% (v/v) sorbitan monooleate (SPAN® 80) in hexanes and saturated with semagacestat is used as the dispersant. The parameters used in the analysis are as follows: sample refractive index—1.555, sample absorption—0.1, dispersant refractive index—1.37, result calculation model—General purpose, normal sensitivity, sample measurement time—12 seconds, background measurement time—12 seconds, and stirrer/pump speed—2700 rpm. A dry sample is added to the Hydro 2000S wet module with sonication on at 100%, until the obscuration is between 10 and 20%. The sample is sonicated for 12 s and stirred for a total of 2 min (including sonication) prior to the analysis. Two separate assays are typically run; the average values are reported.

Determination of Specific Surface Area

Specific surface area is determined from BET isotherm measurements using nitrogen as the absorbed gas.

Optical Microscopy

Optical microscopy and image analysis is used to measure the width and length for a distribution of particles and determining the aspect ratio using Clemex Image Analysis. Specifically, transmitted light optical microscopy is used to determine aspect ratio. Photomicrographs are taken of multiple fields of view. At least six fields of view are analyzed. Particle length and width are measured per particle for multiple selected particles captured in the photomicrographs to calculate an approximate aspect ratio. At least 20 to 50 particles per view are analyzed.

Determination of Particle Flowability

Particle flowability is characterized using a Schulze shear cell tester with a pre-consolidation pressure of 2000 Pa. The powder sample is contained in an annular shear cell. A vertically acting force is applied to the lid of the flow cell allowing an adjustable normal stress to be applied. The shear cell is slowly rotated and the torque necessary to prevent the cover from rotating is recorded. The measured shear stress that is recorded is the shear stress required for the powder to move or flow against itself. From a plot of the shear stress versus normal force, the flowability or FFC is determined

TABLE 2

| | Process | $x_{10}$ (µm) | $x_{50}$ (µm) | $x_{90}$ (µm) | SSA ($m^2/g$) | FFC | Aspect Ratio Range |
|---|---|---|---|---|---|---|---|
| Example 1 | Present Invention | 14 | 59 | 128 | 0.4 | 3.8 | ~2:1 to 5:1 |
| Method 2 | Traditional Crystallization | 3.5 | 17 | 54 | 1.1 | 2.0 | ~5:1 to 20:1 |

Table 2 illustrates particle size and flowability for crystals of semagacestat made via the process of the present invention (Example 1) and traditional crystallization method (Method 2).

Tablet Weight Variation

Tablet weight variation can be used in place of Content Uniformity testing, provided that the dosage strength is greater than 25 mg, the drug loading is greater than 25%, and if the concentration relative standard deviation is not more than 2.0%. USP32/NF27, Chapter 905 (2009). Tablet weight variation is determined by weighing at least ten tablets on an analytical balance and comparing the relative standard deviation of the measurement against established acceptance limits. The relative standard deviation is determined according to:

$$RSD = \frac{100}{\overline{X}} \left[ \frac{\sum_{i=1}^{n} (X_i - \overline{X})^2}{n-1} \right]^{\frac{1}{2}}$$

where $X_i$ is the weight of tablet, $\overline{X}$ is the mean weight of all the tablets, and n is the total number of tablets weighed. In order to meet USP content uniformity criteria (USP32/NF27) 99.9% of the time, the RSD limit is 3.39%. See Rohrs, et. al., J. Pharm. Sci., 95(5), 2006.

All tablets were prepared on a Korsch XL 100® tablet press. The tablets were prepared using a formulation shown in Table 4. The drug loading or amount of semagacestat per tablet is 35% by weight in tablets with a total tablet weight of 400 mg.

TABLE 3

| Run | | Tabletting Speed (RPM) | Tablet Weight Variation |
|---|---|---|---|
| Example 1 | A | 45 | 0.6% |
| Example 1 | B | 70 | 0.7% |
| Method 2 | | 40 | 4.3% |

Table 3 illustrates drug loading and tablet weight variation for tablets made from crystals of semagacestat made via the process of the present invention (Example 1) and traditional crystallization methods (Method 2). Crystals of Example 1 exhibit a lower tablet weight variation within the acceptable ranges for formulation standards. Crystals of Method 2 exhibit a higher tablet weight variation that falls outside of the acceptable ranges for formulation standards.

The variation of tablet weight variability with tabletting speed (or the rotation rate of the tablet press) is also significant. In the case of crystals of Example 1, the highest tablet speed of 70 RPM showed little impact to the tablet weight variation. In the case of crystals of Method 2, the tablet weight variability is outside of acceptable limits even at the lowest tabletting speed. As the tabletting speed increases, powder flowability becomes an important factor in table weight variability; the powder must freely flow into the tablet press faster than the tabletting speed. The higher speed of 70 RPM is representative of the high speed tablet presses used in commercial tabletting operations. Tabletting at lower speeds in commercial manufacturing is not desirable and in many instances, is not a feasible option.

Formulation

TABLE 4

| Ingredient | Quantity (mg/unit dose) |
|---|---|
| Active Ingredient | |
| Semagacestat anhydrate form II | 140.0 |
| Intragranular Powders | |
| Mannitol | 95.0 |
| Microcrystalline Cellulose | 95.0 |
| Croscarmellose Sodium | 16.0 |
| Magnesium Stearate | 4.0 |
| Extragranular Powders | |
| Microcrystalline Cellulose | 40.0 |
| Colloidal Silicon Dioxide | 2.0 |
| Croscarmellose Sodium | 4.0 |
| Magnesium Stearate | 4.0 |

Table 4 illustrates a formulation of a tablet containing semagacestat.

I claim:

1. Crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II characterized by a crystal habit having an average length-to-width aspect ratio of less than or equal to 5:1 and a particle size distribution wherein the $x_{10}$ is less than 50 μm, the $x_{50}$ is less than 100 μm, and the $x_{90}$ is less than 250 μm.

2. The crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II of claim 1 characterized by a crystal habit having a median particle size of 25 to 100 μm, wherein the $x_{10}$ is greater than 4 μm.

3. The crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II of claim 1 wherein the average length-to-width aspect ratio is less than or equal to 3:1.

4. The crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II of claim 2 wherein the average length-to-width aspect ratio is less than or equal to 3:1.

5. A pharmaceutical formulation comprising crystalline (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide anhydrate Form II of claim 1, and a pharmaceutically acceptable carrier, diluent, or excipient.

6. A pharmaceutical formulation of claim 5 wherein the drug loading is 30% or greater and the tablet weight variation is 3.39% or less.

* * * * *